United States Patent [19]

Bowen et al.

[11] Patent Number: 5,461,481
[45] Date of Patent: Oct. 24, 1995

[54] SYSTEM, APPARATUS AND/OR METHOD FOR ANALYZING LIGHT INTENSITIES OF LIGHT REFLECTED FROM A SURFACE OF A SAMPLE

[75] Inventors: Howard Bowen, Northbrook; John S. Little, Glenview, both of Ill.

[73] Assignee: Research Technology International Company, Lincolnwood, Ill.

[21] Appl. No.: 997,872

[22] Filed: Dec. 29, 1992

[51] Int. Cl.⁶ ..................................................... G01N 21/89
[52] U.S. Cl. ...................... 356/430; 250/559.45; 356/431
[58] Field of Search ....................................... 356/430, 429, 356/431, 237; 250/572, 571

[56] References Cited

U.S. PATENT DOCUMENTS

| | | | |
|---|---|---|---|
| 4,652,124 | 3/1987 | Bowen et al. | 356/237 |
| 4,652,125 | 3/1987 | Bowen et al. | 356/237 |
| 4,687,943 | 8/1987 | Bowen et al. | 250/570 |
| 4,786,177 | 11/1988 | Beckstein et al. | 356/430 |
| 4,900,942 | 2/1990 | Rumler | 356/430 |
| 5,130,555 | 7/1992 | Suzuki et al. | 356/237 X |

FOREIGN PATENT DOCUMENTS

| | | | |
|---|---|---|---|
| 62-263453 | 11/1987 | Japan | 250/571 |
| 63-162511 | 1/1988 | Japan | 250/572 |

*Primary Examiner*—Vincent P. McGraw
*Attorney, Agent, or Firm*—Hill, Steadman & Simpson

[57] ABSTRACT

A system, apparatus and/or method for detecting and analyzing light intensities of reflected light from a surface of /a specimen, preferably a web, wherein light is directed onto the surface of the specimen, light reflected from the surface is detected by an array of photosensitive elements, and a signal generated by the array is analyzed to identify reflected light intensities that exceed at least one threshold for a sufficient number of photosensitive elements to warrant classification as indicative of a sufficiently pronounced change in the angularity or reflectance in the surface of the specimen. In particular, the pronounced change can be identified as a defect, for example, a crease, in the specimen surface. Preferably, the array is a CCD array. Preferably, the specimen is a video tape.

38 Claims, 5 Drawing Sheets

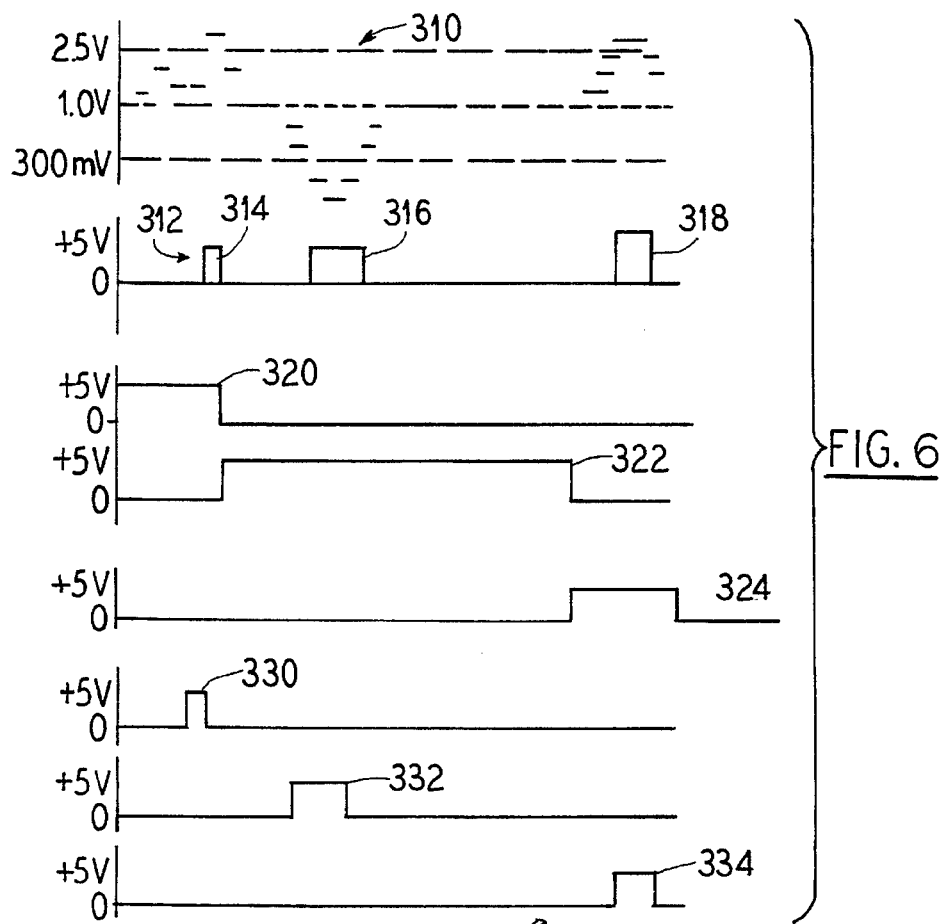
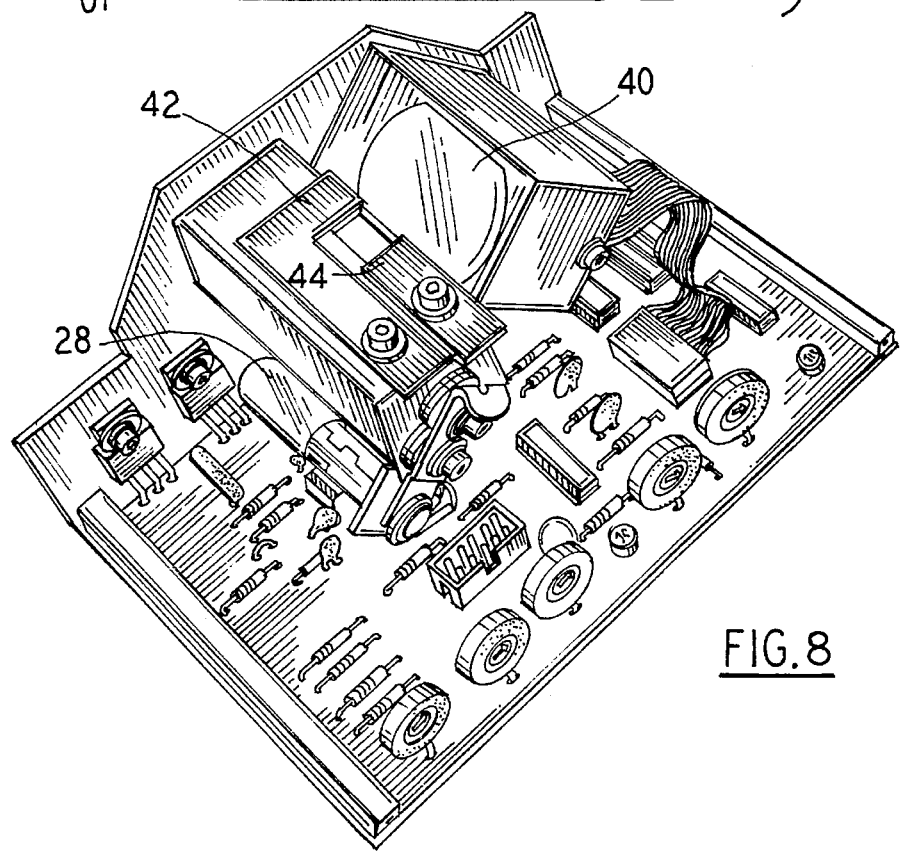
FIG. 8

SYSTEM, APPARATUS AND/OR METHOD FOR ANALYZING LIGHT INTENSITIES OF LIGHT REFLECTED FROM A SURFACE OF A SAMPLE

BACKGROUND OF THE INVENTION

The present invention generally relates to systems, apparatus and/or methods for detecting physical characteristics of samples. More particularly, the invention relates to systems, apparatus and/or methods for detecting physical irregularities or imperfections in webs. Yet more particularly, the invention relates to systems for detecting physical irregularities or imperfections in recording tapes, for example, video tapes.

The assignee of the present invention, Research Technology, Inc., has been selling systems for detecting physical irregularities or imperfections in recording tapes, specifically video tapes. In these systems, a video tape is reviewed and evaluated for physical damage in the form of, for example, holes, creases, scratches, et cetera.

As a general rule, in such systems, light is directed onto a section of the tape and reflected light is received by one or more photocells which then generate signals containing information concerning the nature of the surface of the tape section under examination. In this regard, a tape surface ideally is smooth. Light reflected from the smooth surface generally will reflect at an angle equivalent to that of the incident light. However, if an irregularity such as a crease or a hole is present on the surface of the tape, then the light will reflect at a different angle.

If a photocell is positioned at the expected angle of reflection, a smooth surface will reflect the incident light evenly toward the photocell. However, a damaged surface will reflect the light unevenly such that the photocell will detect either an increase (bright spot) or decrease (shadow) in reflected light.

Although such prior art systems basically have worked well for their intended purpose, there is room for improvement. In particular, because a photocell is a discrete device, it is incapable of discriminating between portions of the surface of a tape, i.e. the resolution is low. Accordingly, information about the physical characteristic of the surface of the tape can only be generated for large defects.

SUMMARY OF THE INVENTION

The present invention provides a system, apparatus and/or method for analyzing light intensities of light reflected from a surface of a specimen to detect a physical characteristic of the sample. Additionally, the invention provides a system, apparatus and/or method for detecting a physical characteristic of a web. Yet more specifically the invention provides a system, apparatus and/or method for detecting a physical characteristic of a recording tape.

To these ends, in an embodiment, the invention provides a system for analyzing light intensities of light reflected from a surface of a specimen comprising a detector having a light source positioned to direct light onto the surface and a sensor positioned to detect the light reflected from the surface, the sensor having an array of photosensitive elements that serve as an array of cell elements and configured to generate a detection signal containing information about the light intensities of the light reflected from the surface sensed by each cell; and a processor coupled to the sensor, the processor being configured to receive and analyze the detection signal to identify a sufficient number of cells whose sensed light intensities transgress a threshold to warrant a classification as an extraordinary reflection of light.

As used herein, an extraordinary reflection of light can be too much reflected light (bright spots) or too little reflected light (shadows). Extraordinary reflections of light generally can be considered as resulting from a physical defect in the surface such as a crease, fold, hole, bump, et cetera.

As also used herein, the transgression of a threshold is used to mean the exceeding of an upper threshold or level as well as the falling below of a minimum threshold or level. Further, since the rate of scanning of the cells and velocity of a moving surface can be predetermined, the area of a moving surface scanned by one cell during one scanning interval can be defined as one pixel. A pixel then represents a rectangular area on the surface.

In an embodiment, the invention provides that the processor is configured to compare the sensed reflected light of each pixel to two thresholds, one threshold being above an average light intensity, and the other threshold being below an average light intensity and to identify transgressions of either threshold.

In an embodiment, the invention provides that the sensor is a charged coupled device (CCD) array.

In an embodiment, the invention provides that the output of the sensor is divided into timed segments, each timed segment being time allocated to a different portion of the surface of the specimen.

In an embodiment, the processor is configured to identify transgressions of a threshold within each timed segment of the output of the sensor.

In an embodiment, the invention provides that the intensity of the lamp is regulated such that the long term average reflected light intensity is held constant.

In an embodiment, the invention provides that the thresholds are set to be deviations from the average reflected light intensity.

In an embodiment, the specimen is a web.

In an embodiment, the specimen is a recording tape.

In an embodiment, the recording tape is a video tape.

In an embodiment, a lens is positioned between the sensor and the web so as to direct a segment of the web onto the sensor.

In an embodiment, the sensor is a CCD array, and the lens directs a transverse segment of the web onto an entire length of the CCD array.

These and other features of the invention will become clear below with reference to the following detailed description of the presently preferred embodiments and accompanying drawings.

BRIEF DESCRIPTION OF THE DRAWINGS

FIG. 6 illustrates graphs of various signals that can be present during operation of the circuit of FIGS. 5, 6 and 7.

FIG. 8 illustrates a perspective view of an apparatus embodying features illustrated in FIGS. 1–7.

DETAILED DESCRIPTION OF THE PRESENTLY PREFERRED EMBODIMENTS

As discussed above, the present invention provides a system, apparatus and/or method for analyzing light intensities of light reflected from a surface of a specimen for identifying a physical characteristic of the specimen. The invention arose in the context of a system for inspecting video tapes for physical damage thereto and it is in that context that the following description is made. However, the following description is only by way of example and the invention is not to be taken as limited to the field of video tape inspection.

With the foregoing caveat, in the Figures, there is illustrated an embodiment of the invention particularly suited for the inspection of a web, specifically a recording tape such as a video tape. The following description is made with reference to the Figures.

As will become clearer below, the present system or apparatus can be broken down into two basic sections or portions. The first section is a detection section 10 which is employed to detect or sense light emanating from the surface of a specimen or sample and to generate a detection signal with information relating thereto. The other section is a processor section 12 which is used to receive and analyze the detection signal. the detection section 12 in turn then generates a number of signals with information relating to the analysis of the detection signal.

Figure 1:
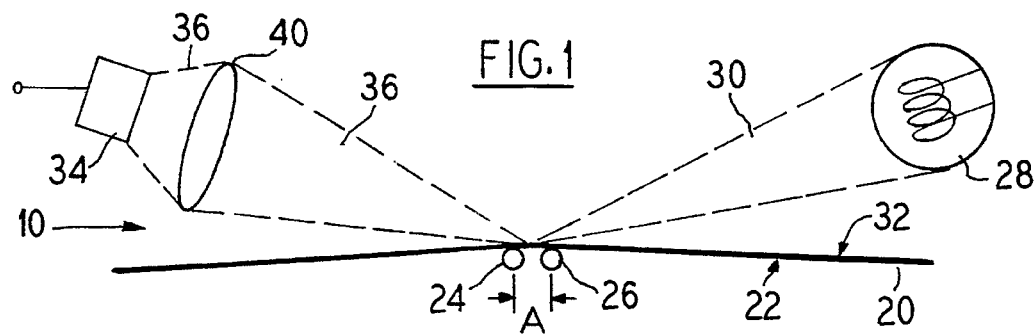
FIG. 1 illustrates in schematic form, a detection section of a system embodying principles of the invention.

In FIG. 1 there is illustrated in schematic form the detection section 10 for producing the detection signal relating to the physical character of a web 20, in this case, a magnetic recording tape. As illustrated, the tape 20 is aligned and supported on one side 22, the non-recording side, by a pair of support members 24 and 26. A light source 28 is positioned on an opposite side of the tape 20 so that light 30 emitted by the light source 28 is directed onto the recording surface 32 of the tape 20.

The light source 28 preferably is a small, high-quality incandescent lamp. However, ideally, the light source would be a point of light centrally positioned along the web 20.

The support members 24 and 26 preferably comprise a pair of sapphire rods. Sapphire rods are preferred because of their hardness and smoothness upon polishing, and thus their durability. Further, they cause less wear on the tape 20 as the tape runs thereover.

As can best be appreciated from FIG. 1, the support members 24 and 26 are spaced apart from each other. Moreover, the members 24 and 26 serve to extract the tape 20 from its cassette (not shown) such that the tape 20 is pulled therefrom. The distance separating these members is determined empirically. The distance of separation must not be so short that the tape 20 is held too tautly thereby ironing out the defects, for example, creases in the tape 20, during the inspection. On the other hand, the distance of separation must not be so long so that minor defects are amplified due to bending of the tape 20. In the preferred embodiment, the distance of separation between the support members 24 and 26 is approximately ¼".

As further illustrated, a light receiver or sensor 34 is positioned to receive light 36 reflected from the surface 32 of the tape 20. In the preferred embodiment, the light receiver 34 is a CCD array having a linear array of 64 light sensitive elements or photoreceptors. The CCD array is employed to generate the detection signal comprised of a series of pulses, which are further processed by the processor section 12.

It can be appreciated that due to the configuration of a CCD array, each of the 64 photoreceptors can be considered a cell, and as such, the detection signal generated by the CCD array contains cell data. In the illustrated embodiment, the datum for each cell comprises a pulse whose amplitude is determined by the intensity of the sensed reflected light. When scanned, each cell produces an image pixel. A hypothetical signal output by the CCD array 34, comprising a series of pulses having different amplitudes, i.e., stepped pulses, is illustrated as signal 300 in FIG. 7.

During operation, the tape 20 preferably is passed under a detection footprint at a rate of about 120 inches per second. The detection footprint is that area within the sensing field of the CCD array 34. A pixel array is formed by the timing of the scans of each cell along the footprint.

As discussed further below, the CCD array preferably is driven at a rate of 320 kilohertz. This in turn translates into a scan time of about 200 microseconds per scan or scan line and approximately 3.125 microseconds per pixel.

It can be appreciated, therefore, that during one scan line, i.e. 200 microseconds, the tape will advance 24 thousandths of an inch. Thus, each scan will occur over a line substantially transverse but slightly skewed with respect to the tape 20 that has an angle that deviates by 24 thousandths of an inch from top to bottom, forming a skewed array of 64 pixel elements 0.024 inch wide.

As will be described in greater detail below, in the processing of the detection signal generated by the CCD array, the detection signal is analyzed to identify light intensities that transgress either an upper threshold (bright spots) or a lower threshold (shadows). This is accomplished by identifying those pulses in the detection signal whose voltages exceed or fall below respective threshold voltages.

Figure 2:
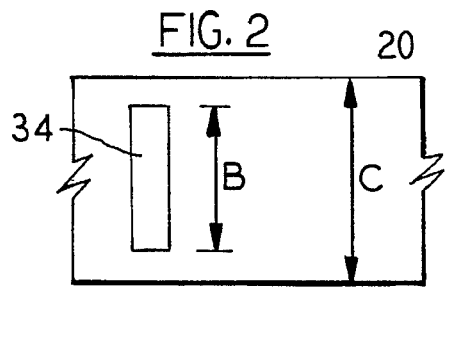
FIG. 2 illustrates a size relationship between a detector array and a ½" video tape.

As illustrated best in FIG. 2, it can be seen that a 64 element CCD array has a length of about 0.30 inches. Yet a video tape can have a different width, e.g., a width of about ½ inch. Thus, it is apparent that such a CCD array cannot be used to sense directly light reflected across an entire ½ inch width of tape since reflected rays diverge even up to approximately one (1) inch within 1–2 inch distance from the surface of the tape.

To overcome this discrepancy, in the preferred embodiment, a plane convex lens 40 is positioned between the CCD array and the tape surface so as to direct the light reflected from nearly the entire ½ inch width of the tape onto the 0.30" long CCD array 34. For purposes that will become apparent below, the outer edges of the tape 20 are not inspected and, thus, the lens 40 focuses an area slightly inward of both edges of the tape 20 onto the length of the CCD array 34.

The span of the tape which actually is subject to inspection is determined empirically, i.e., by experiment and judgment. At the present time, test results are obtained by adjusting the focal length of the lens so that an overall central portion of the tape 20 is scanned, i.e., only small outer edge strips are not scanned.

Another feature of the embodiment illustrated best in FIG. 8 is the provision of shutters to reduce the footprint of the light from the light source 28 on the surface 34 of the tape 20. These shutters, which are illustrated in FIG. 8, preferably comprise two plates 42 and 44 that are adjustably positioned between the tape 20 and the light source 28 and on opposite edges of the tape 20 to create a window that can be altered in size as needed, thereby to alter the size of the footprint of light on the tape 20. The appropriate size of the footprint is determined empirically but preferably has edges resulting slightly inward of the lateral edges of the tape 20. Thus, reflections from the tape edges are eliminated and consequently so are inadvertent bright spots and shadows created by bending of the edges of the tape 20 as it runs past the detection footprint.

Figure 3:
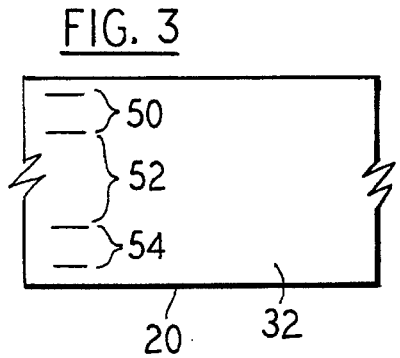
FIG. 3 illustrates delineation of scanned areas of a ½" video tape.

With reference particularly to FIG. 3, it can be seen that in order to more accurately pinpoint defects in the tape 20, provision is made for subdividing the tape into sections. To this end, the width of the tape 20, and consequently the cells of the CCD array 34, are subdivided into three sections: an upper section 50, a center section 52 and a lower section 54. As the nomenclature implies, a certain number of CCD array cells are dedicated to scanning the upper section or strip 50 of the tape 20, while other cells are dedicated to the scanning center and lower sections 52 and 54 of the tape 20, respectively. The CCD array 34 thus preferably is subdivided so that 12 cells on each end of the array are dedicated to scanning the upper and lower sections 50 and 54 of the tape 20 while the central 40 cells are dedicated to scanning the center section 52 of the tape 20.

It can be appreciated that the 64-element CCD array 34 contains a linear array of 64 photosensing elements, and, thus, the CCD array 34 provides photosensing at 64 positions within the 0.30" span of the array. Because the array is not positioned directly on the surface of the tape, but instead is positioned at some distance therefrom, light from one position along the tape can be sensed to a degree by more than one photosensor element of the CCD array 34. Thus, the CCD array 34 essentially can sense light reflected from across the entire span established by the lens 40, but still discriminate between 64 discrete locations.

Figure 4:
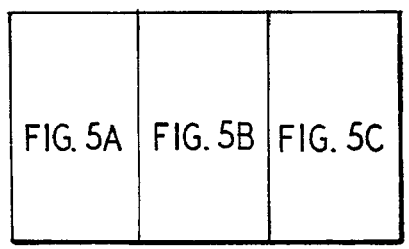
FIG. 4 illustrates the relationship between FIGS. 5A, 5B and 5C.
Figure 5A:
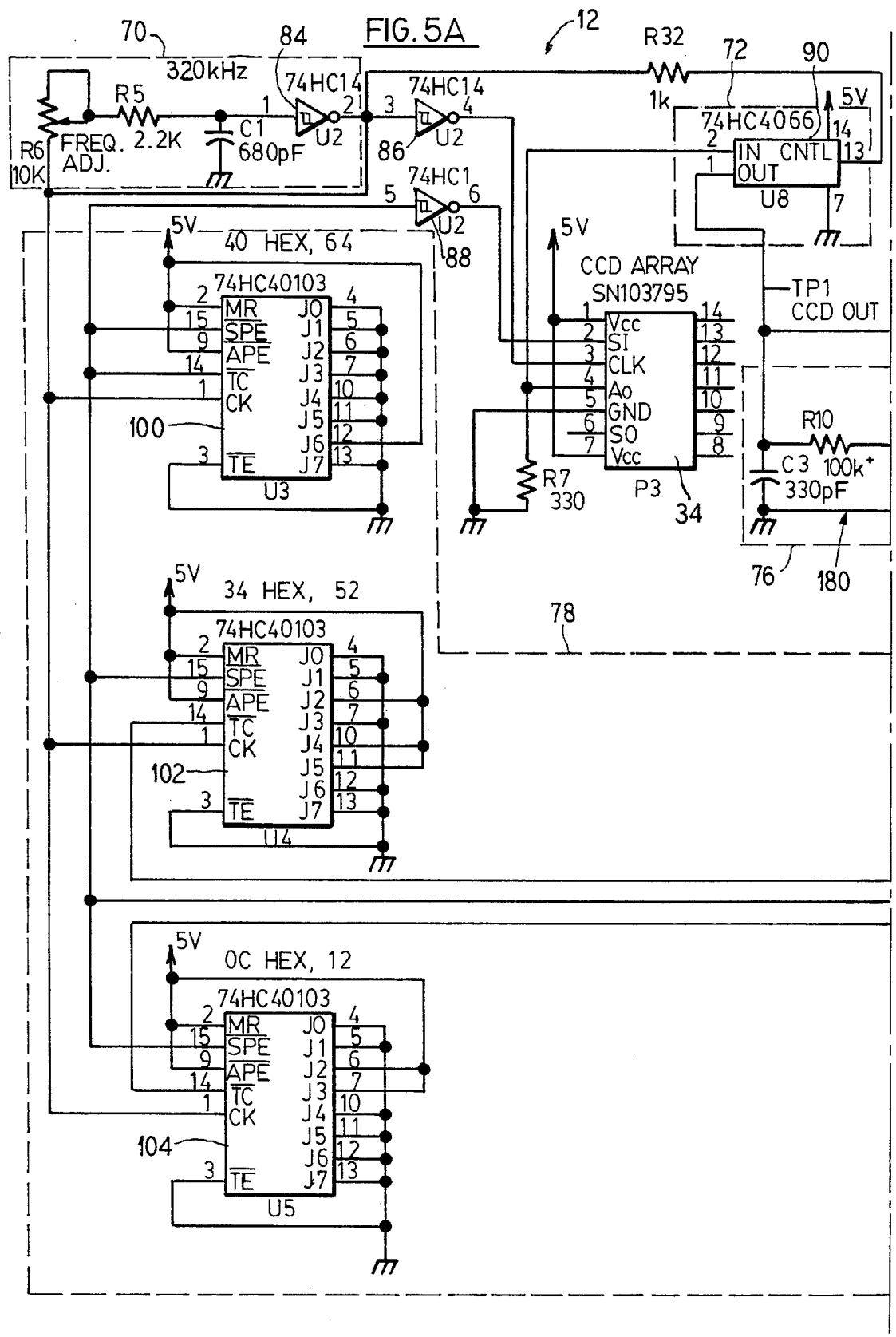
FIGS. 5A, 5B and 5C illustrate a circuit diagram of a processor section for receiving and analyzing a detection signal generated by the detection section of FIG. 1.
Figure 5B:
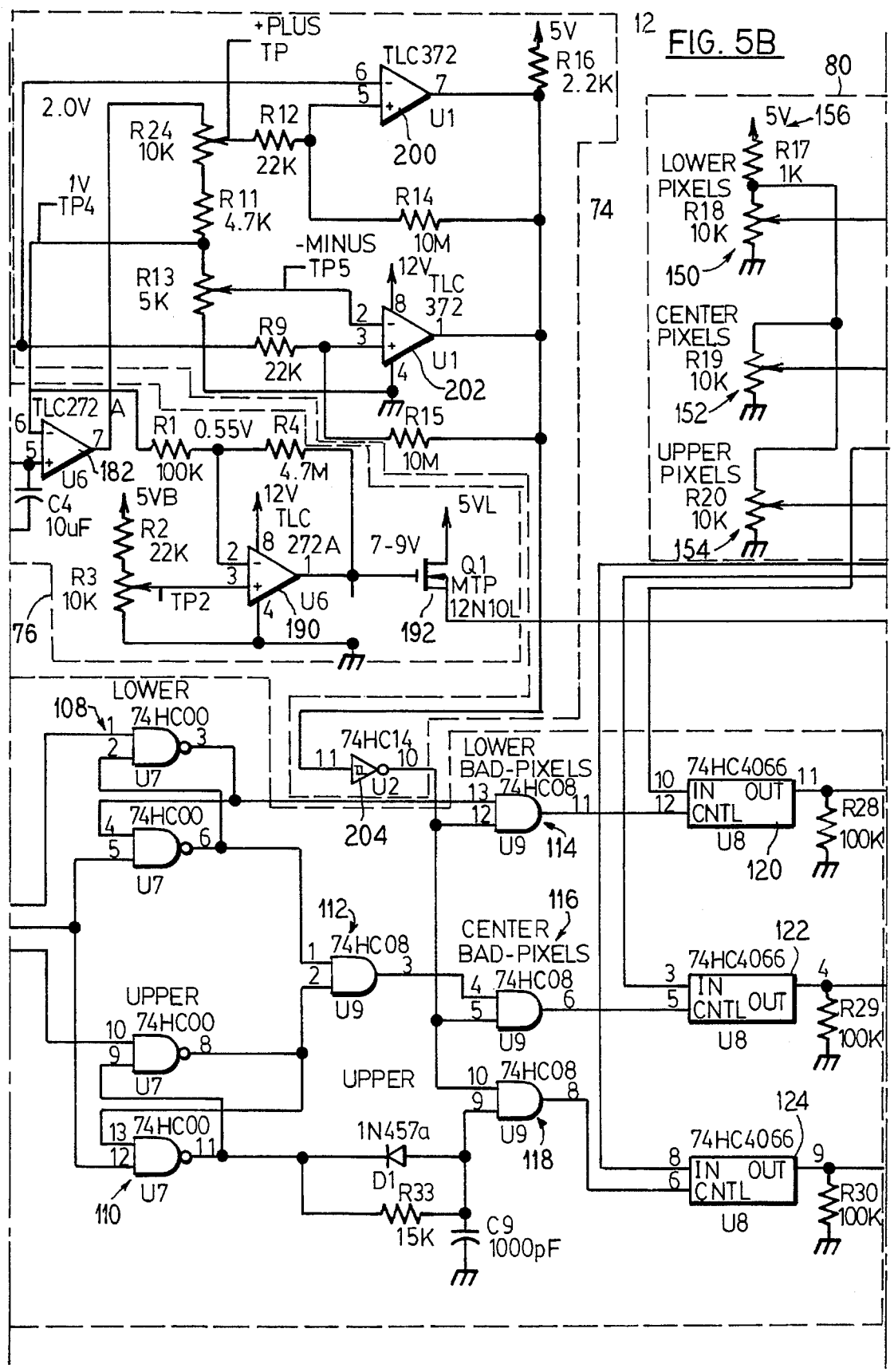
Figure 5C:
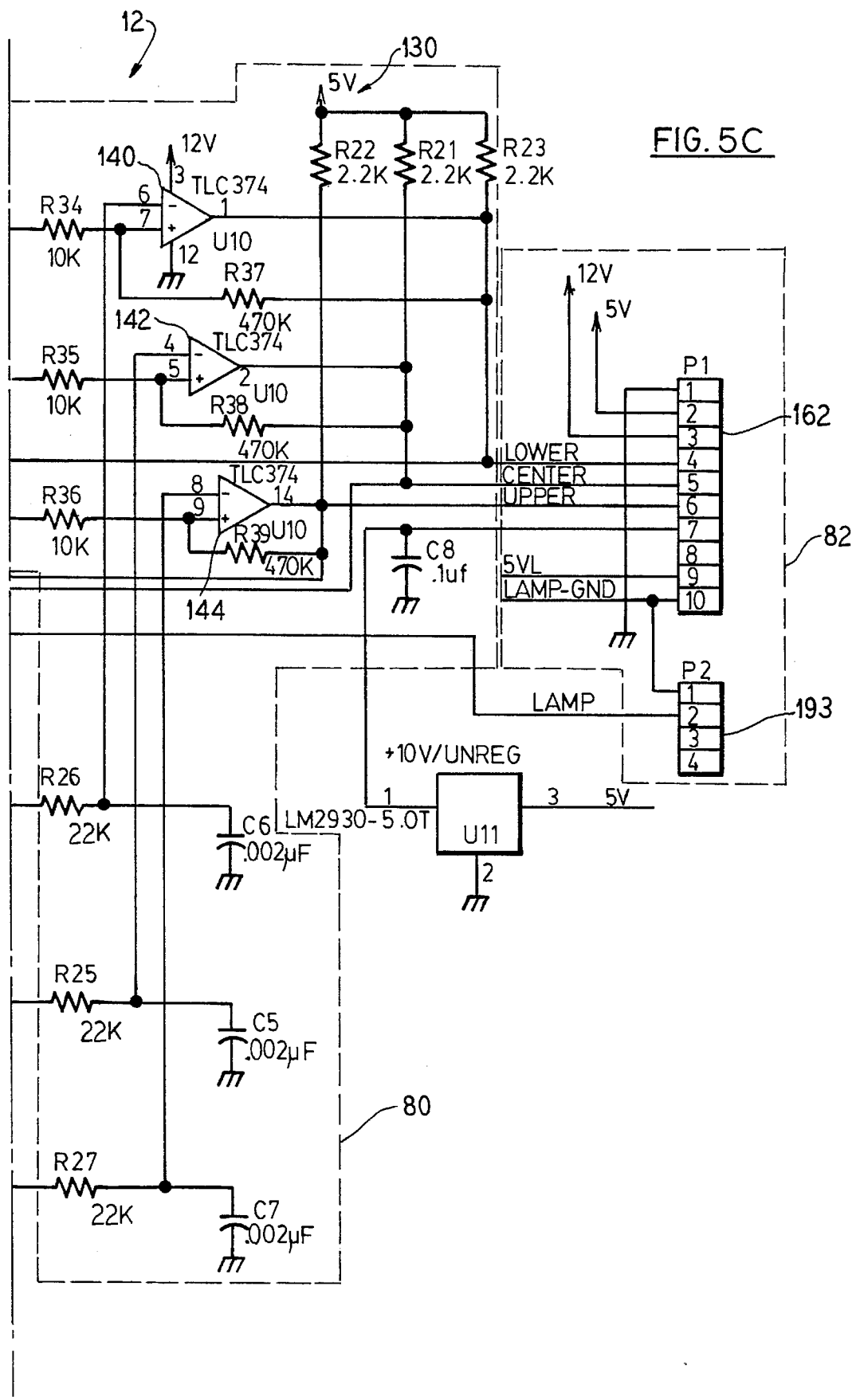

In FIGS. 5A, 5B and 5C, there is illustrated a circuit diagram for the processor section 12. The manner in which FIGS. 5A, 5B and 5C interrelate is illustrated in FIG. 4.

As illustrated, the processor section 12 can be subdivided into seven major subsections: an oscillator 70, a detection signal gate 72, a threshold transgression detection circuit 74, a lamp driver circuit 76, a detection signal to specimen section correlation circuit 78, a threshold transgression filter 80 and an output section 82.

As discussed above, the oscillator 70 is configured to produce a clocking signal having a frequency of about 320 kHz. This clocking signal then is used to drive components of the processor section 12 and the CCD array 34 so that the entire system is run with coordinated timing. The oscillator 70 is comprised of resistor R3, variable resistor R6 (for frequency adjustment), capacitor C1 and Schmitt trigger 84.

As one feature of the circuit of the processor section 12, the clocking signal generated by the oscillator 70 is coupled to the control input of an analog switch 90 by way of resistor R32, which form the detection signal gate 72. The analog input of the switch 90 is directly coupled to the output of the CCD array 34 so that the detection signal generated by the CCD array 34 is directed to and received by the processor section 12 via the analog switch 90. The output of the switch 90 then is directly coupled to inputs of the threshold transgression detection circuit 74 and lamp driver circuit 76. It can be appreciated that the detection signal thus is directly gated to these latter two circuits 74 and 76 by way of the analog switch 90 at a rate of about 320 kHz. The functions of these circuits 74 and 76 are discussed in greater detail below.

Figure 7A:
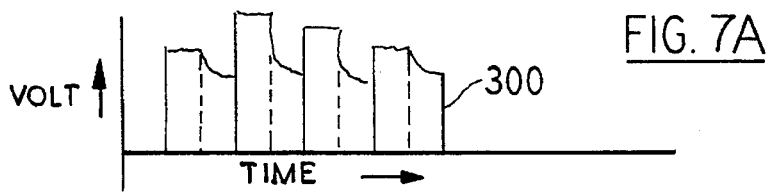
FIG. 7 illustrates a detection signal generated by the detection section of FIG. 1 and an adjusted version thereof for use by the processor circuit of FIGS. 5A, 5B and 5C.
Figure 7B:
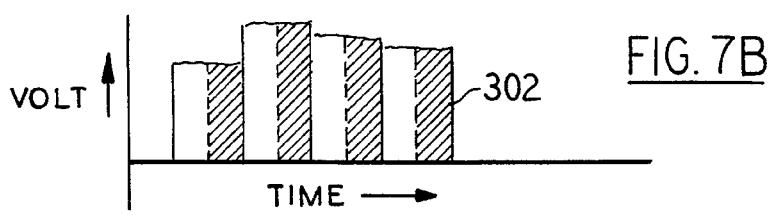

In FIG. 7 it is illustrated how the detection signal output by the CCD array 34 is conditioned by the interposition of the analog switch 90 between the CCD array 34 and the inputs to the circuits 74 and 76 to make it crisper and more defined for easier processing by the processing circuitry of FIGS. 5A, 5B and 5C. As illustrated, the direct output 300 of the CCD array 34 is not even over each cell scan, but instead rises and falls over the cell scan. Essentially, only the first 50% of each pulse resulting from a cell scan contains useful information as the second 50% becomes too degraded. The result is a pulse for each cell scan that has a stair-step shape.

To clean up the output, the second 50% of each pixel pulse is eliminated by means of the analog signal switch 90. Commencing at the beginning of the output of each CCD output pulse, i.e., when its output is highest, the switch 90 allows the signal to pass through to circuits 74 and 76, where the signal charge is stored on capacitor C3. This is accomplished by the switch 90 being switched at the 320 kHz rate directly from the oscillator 70 while the CCD array 34 is clocked after a delay by the Schmitt trigger 86. Then about halfway through each readout, the analog switch 90 is turned off and the trailing second half of each pixel pulse is cut off and replaced by the charge stored in capacitor C3. Because the charge stored on capacitor C3 is equal in value to the charge present in the first half of the original pulse, the resulting adjusted pulse includes a full pulse whose second half is not degraded. The result is a signal 302 comprised of a series of stepped pulses whose second halves are not degraded, as illustrated in FIG. 7.

Before the remainder of the processor section 12 is discussed, the manner in which the upper, center and lower tape sections, 50, 52 and 54, are identified should be discussed. In this regard, in the scan of the CCD array 34, the delineation between the upper, center, and lower scan sections 50, 52 and 54 is made by the setting and resetting of various flip-flops in the detection signal to specimen correlator circuit 78.

To this end, there are coupled to the oscillator 70 three counters 100, 102 and 104. The first counter 100 is configured to count up to 64 and then reset to zero, continuously. The second counter 102 is configured to count up to 12 and then remain in an off position until reset by the resetting of the first 64-count counter 100. The third counter 104 is configured to count up to 52 and then remain in an off state until reset by the first 64-count counter 100.

The CCD array 34 also is reset after every count of 64 by counter 100 via Schmitt trigger 88. Resetting of the CCD array 34 causes sequencing of the output signal to commence with the first pixel, etc.

It can be appreciated that with the foregoing counters, at least three distinct time periods can be established; namely, a first time period during which all of the counters 100, 102 and 104 count from zero to twelve, a second time period during which just the first and third counters 100 and 104 count from thirteen to fifty-two, and a third time period during which just the first counter 100 continues to count from fifty-three to sixty-four. The result is that a sequence of three time periods of twelve, forty and twelve can be established, and these three time periods correlate to the three scan times of the first twelve, middle forty and last twelve cells of the CCD array 34.

The outputs of these counters are then used to drive various flip-flops. This can be seen in FIG. 5B.

As illustrated in FIG. 5B, a first flip-flop 108 is used to identify the time period correlated with scanning of the lower cells while a second flip-flop 110 is used to identify the time period correlated to scanning of the upper cells. These flip-flops will generate a logical 1 or HIGH when the counters are at the count corresponding thereto. It is assumed that if neither the lower cells nor the upper cells are being scanned, then the center cells are being scanned, and this determination is made by AND gate 112. The outputs of these flip-flops 108 and 110 and AND gate 112 are coupled to three AND gates 114, 116 and 118 thereby to appropriately correlate portions of each scan that exceed a threshold with the appropriate set of cells.

To that end, additionally coupled to each of the AND gates 114, 116 and 118 is the single output signal from the threshold transgression detection circuit 64. The outputs of the AND gates 114, 116 and 118 are directed to the analog inputs of respective analog switches 120, 122 and 124.

As illustrated, the output of these AND gates 114, 116 and 118 are used to control switching on the respective switches 120, 122 and 124. To that end, the outputs of the AND gates 114, 116 and 118 are connected to the control inputs of the switches 120, 122 and 124. The analog inputs of the switches are coupled to a 5 V voltage source 130 via respective resistors R22, R21 and R23 while the outputs are coupled to respective charging capacitors C6, C5 and C7 in the threshold transgression filter 80 via respective coupling resistors R26, R25 and R27. The capacitors C6, C5 and C7 are selected such that a minimum of a total of about 9 milliseconds of charging time is required to charge them, i.e., one of the thresholds must be exceeded for at least three pixel scans before the respective capacitor is sufficiently charged. The three pixel periods need not be contiguous, i.e., if, for example, the first, second and fifth cells detect excessive light, then the minimum number will have been met. Additionally, the threshold exceeding pixel periods need not occur on the same scan, e.g., if the first cell detects excessive light for two scans and the second cell detects excessive light in a third scan, then the minimum number also will be met. Due to the minimum charging time of these capacitors C6, C5 and C7, they act as the threshold transgression filter circuit 80 by requiring a minimum number of threshold transgressions before an error is recognized by the processor circuit 12.

Resistors R28, R29 and R30 serve to discharge the capacitors C6, C5 and C7 slowly to prevent long term accumulation of charge.

As also illustrated, the filtered outputs of the switches 120, 122 and 124 are also tied to the minus inputs of respective comparators 140, 142 and 144 so that as the charge on one of the capacitors C6, C5 and C7 builds up, the voltage input to the respective comparator 140, 142 or 144 is also increased.

The plus inputs of the comparators 140, 142 and 144 are coupled to respective voltage dividers 150, 152 and 154. These voltage dividers comprise variable resistors R18, R19 and R20 tied to a 5 V voltage source 156, and whose taps are coupled to the plus inputs of the comparators 140, 142 and 144, respectively, so as to establish reference voltages preferably equal to at least the voltage on the respective capacitors C6, C5 and C7 after charging for three pixel periods. The outputs of the comparators 140, 142 and 144 are tied to a logical 1 or HIGH by means of respective pull-up resistors R23, R22 and R21 coupling the outputs to the 5 volt source 130. Thus, charging of capacitors C5, C6 and C7 essentially also is accomplished by means of the output of the comparators 140, 142 and 144 being connected to the inputs of analog switches 120, 122 and 124, respectively.

It can be appreciated that when charge builds up on one of the capacitors C6, C5 or C7 so as to exceed the voltage established by its respective voltage divider 150, 152 or 154, the respective comparator 140, 142 or 144 will be caused to generate an output signal, in this case a negative voltage transition which essentially ties the 5 volt source 130 to ground. As a result, a digital logical signal of 0 or LOW appears at the output of the comparator 140, 142 or 144 in question, and thus at the input of the respective analog switch 120, 122 or 124.

As further illustrated, the outputs of the comparators 140, 142 and 144 are directed to the output section 80 which comprises an output connector strip 160 at which point a further processor can read the information signals being generated and react as desired. For example, a further processor could generate a report identifying those areas of the tape under test for which physical defects were identified.

Feedback resistors R37, R38 and R39 are respectively coupled between the outputs and the plus inputs of comparators 140, 142 and 144, respectively, to eliminate the possibility of double counts of defects. Essentially, these resistors make the comparators 140, 142 and 144 behave like Schmitt triggers.

To this end, these resistors R37, R38 and R39 provide charging paths which serve to quickly change the outputs of the respective comparators 140, 142 and 144 back to a logical 1 or HIGH so that on the next scan, despite slowness in the discharge of the capacitors C6, C5 and C7, an extraordinary intensity, i.e., a defect, is still not indicated. As can be seen, charging of the capacitor C6, C5 or C7 only occurs while the output of the respective comparator remains HIGH.

Another feature of the circuit of FIGS. 5A, 5B and 5C is the network 76 for regulating the intensity of the lamp 28. In this regard, the intensity of the lamp 28 is regulated such that a relatively long term average intensity response of one (1) volt in the detection signal is produced and maintained. By maintaining a known average response, it is easier to detect variations thereof that represent defects in the tape under review. Minor and inconsequential variations due to, for example, movement of the tape, different tape reflectances, etc. then can be ignored.

This averaging is accomplished as follows: the detection signal generated by the CCD array 34 is gated by the switch 90 to produce the modified or adjusted detection signal 302 comprised of a series of crisp stepped pulses as described above. This modified or adjusted CCD array detection signal then is directed to an averaging network 180 comprised of capacitors C3 and C4 and resistor R10 whose output is coupled to an operational amplifier 182. The response of the filter 180 is set to be about 1 second. Charge builds up on capacitor C4. The output of the operational amplifier 182 is directed to a voltage divider network comprised of variable resistors R24 and R13 and resistor R11.

The voltage present between resistors R11 and R13 is fed back to the minus input of the operational amplifier 182 so that the operational amplifier 182 constantly establishes a reference voltage for threshold transgression comparators 200 and 202, the functions of which are described more fully below.

By matter of design, the value of the voltage between resistors R11 and R13, and hence the voltage provided at the minus input of operational amplifier 182, is set to be about 1 volt. Thus, the instantaneous voltage of the detection signal is adjustably compared to a range of values which range is a function of the average value of the detection signal.

As further illustrated, the signal applied to the minus input of operational amplifier 182 (the average cell output) also is applied to the minus input of another operational amplifier 190 via a resistor R1. The output of operational amplifier 190 is used to drive a power transistor 192, which in turn is used to drive the lamp 28 via output connector strip 193. The plus input of the operational amplifier 190 is coupled to a variable voltage divider network comprising a variable resistor R3 coupled to a resistor R2 coupled to a 5 V source, so that a constant comparison voltage is established at the plus input. It can be appreciated that as the average value of the detection signal increases (i.e., the light intensity increases), the voltage feedback to the minus input of the operational amplifier 182 will increase. In turn, the voltage at the minus input of operational amplifier 190 will increase and this will cause a decrease in the output of operational amplifier 190. Because the output of operational amplifier 190 drives power transistor 192, a decrease in the output of the operational amplifier will cause a decrease in the drive signal to power transistor 192, and thus a decrease in the power for the lamp 28. Conversely, as the average voltage (and therefor the average intensity of the sensed reflected light) decreases, the voltage being applied to the minus input of the operational amplifier 190 will decrease and this will cause and increase in the drive signal to the power transistor 192. As a result, the network 76 self-modulates (i.e., provides an automatic gain control therefor) the intensity of the lamp 28.

The threshold transgression detection circuit 74 essentially is comprised of the pair of comparators 200 and 202 whose outputs are commonly coupled to the input of a Schmitt trigger 204. The input of the Schmitt trigger 204 is normally set at a logical 1 or HIGH by means of 5 V source 206 and pull-up resistor R16.

The comparator 200 is used to detect transgression of an upper threshold, i.e., light intensities in excess of a maximum threshold level while comparator 202 is used to detect transgressions of a minimum or lower threshold, i.e., light intensities falling below a minimum level. In the presently preferred embodiment, the maximum and minimum levels are deviations from the average level of the detection signal, which is maintained at about 1 volt. The deviations are set to about a 70% loss of light or a 150% gain in light. Thus the lower threshold is set to be about 70% less than 1 volt, i.e., 300 mV while the upper threshold is set to be about 150% greater than 1 volt or about 2.5 volts.

To these ends, the modified or adjusted detection signal is fed into the minus input of comparator 200 and the plus input of comparator 204. The plus input of comparator 200 then is coupled to the tap of variable resistor R24. The minus input of comparator 204 is coupled to the tap of variable resistor R13.

It can be appreciated that because the point between resistors R11 and R13 is set to be about 1 volt, the tap of the variable resistor R24 will be higher than the point between resistors R11 and R13 by the amount it is adjusted to, which is by 150% as discussed above. Similarly, the tap of the resistor R13 will be set to be at a voltage 70% less than the point between resistors R11 and R13, i.e., 300 millivolts.

In operation, every time a cell generates a pulse in excess of 50% greater than the average level of the detection signal, i.e., 2.5 volts, then the comparator 200 will pull the input of the Schmitt trigger 204 down to zero volts, i.e., a logical 0 or LOW. When that happens, the Schmitt trigger 204 emits a pulse that is sent to each of the AND gates 114, 116 and 118. Whichever of AND gates 114, 116 or 118 has its other input set to a logical 1 or HIGH by flip-flops 108 and 110 and AND gate 112, will provide a logical 1 or HIGH signal to its respective switch 120, 122 or 124, as set forth above. Thus, one of the capacitors C6, C5 and C7 will be provided with a charge, as set forth above.

Similarly, should a cell detect less than the minimum threshold amount of reflected light (300 millivolts), then, the comparator 202 will be triggered to emit a logical 0 or LOW which in turn will also cause the Schmitt trigger 204 to emit such a pulse.

Whenever a particular one of the capacitors C6, C5 and C7 receives at least three such pulses within its allocated portion of a scan line or successive scan lines, then a fault or defect will be recognized as described above.

In FIG. 6, various signals that can be present in the circuit of FIGS. 5A, 5B and 5C during a scan by the CCD array 34 are illustrated. Signal 310 is but one possible adjusted detection signal output of the CCD array 34 over one 200 microsecond scan. As can be seen in FIG. 7, for the purpose of discussion, it has been hypothesized that the 11th and 12th pixels generated outputs above the 1.5 volt threshold; the 23rd, 24th, 25th, 26th, 27th and 28th pixels generated outputs below the 300 millivolt threshold; and the 58th, 59th, 60th and 61st pixels generated outputs above the 1.5 volt threshold.

Signal 312 would be the signal generated by the Schmitt trigger 204. As illustrated, signal 312 comprises a series of pulses 314, 316 and 318 of equal height but of lengths corresponding to the number of contiguous pixels generating outputs outside of the range defined by the upper and lower thresholds.

Signals 320, 322 and 324 are the signals generated by the flip-flops 108 and 110 and AND gate 118, respectively, in accordance with the counts determined by counters 100, 102 and 104.

Signals 330, 332 and 334 are the signals that would be generated by AND gates 114, 116 and 118, respectively, based on the ANDing of signal 312 with signals 320, 322 and 324. As discussed above, these signals 330, 332 and 334 will cause capacitors C6, C5 and C7 to charge for 2, 6 and 4 pixel periods, respectively. Because capacitor C6 charges only for 2 pixel periods, it will not charge sufficiently to trigger its comparator 140. On the other hand, both capacitors C5 and C7 will charge for the duration of 3 pixel scans or greater and thus will respectively cause comparators 142 and 144 to trigger and generate logical 0 outputs. These outputs can then be interpreted as an indication of physical defects in the surface of sections 52 and 54 of the tape 20, e.g., creases or holes.

As also illustrated in FIG. 5B, a delay network comprised of diode D1, resistor R33 and capacitor C7 is coupled between the output of flip-flop 110 and AND gate 118. This delay network introduces a short delay of a fraction of one pixel scan in the transmission of the change in the output of the flip-flop 110 to the AND gate 118 so that the pixel threshold transgression information does not end up erroneously associated with the lower section 54. This is because, due to the configuration of the illustrated system, it just happens that the output of the first pixel always is low, i.e., below the lower threshold.

Although modifications and changes may be suggested by those skilled in the art, it is the intention of the inventors to embody within the patent warranted hereon all changes and modifications as reasonably and properly come within the scope of their contribution to the art.

What is claimed is:

1. An apparatus for recognizing physical aberrations in a moving web having a smooth reflective surface, comprising:

support means for supporting a section of the web within an inspection zone;

light source means for directing light from a point source of light onto the section of the web;

detecting means for sensing light reflected from the smooth reflective surface of the web and for generating a detection signal correlated to the amount of light sensed, said detecting means comprising a linear array of photosensitive elements arranged transversely relative to the web and said detection signal comprising a series of voltage pulses respectively generated by said photosensitive elements; and processing means for processing the detection signal and identifying an amount of reflected light outside of at least one threshold due to the occurrence of aberrational non-incidental reflection of light, said processing means capable of identifying whether said threshold is exceeded for a predetermined time period so as to be indicative of the presence of a crease along said web.

2. The apparatus of claim 1 wherein said support means comprises a pair of spaced apart support members, said support members being spaced apart by a distance of about one fourth of an inch.

3. The apparatus of claim 2 wherein said support means comprises a pair of sapphire rods.

4. The apparatus of claim 1, wherein said processing means is configured for identifying an amount of reflected light outside of either of two thresholds.

5. The apparatus of claim 1, wherein said processing means is configured to correlate transgressions of the at least one threshold with a section of said web.

6. The apparatus of claim 1, wherein said web is a magnetic recording tape.

7. The apparatus of claim 1, wherein said processing means includes:

an oscillator;

a plurality of counters driven by said oscillator;

a threshold transgression circuit configured to receive said detection signal and to recognize voltage pulses having voltages outside of a limit established by said at least one threshold; and a threshold transgression to specimen section correlation circuit coupled to both said threshold detection circuit and said plurality of counters so as to correlate any detected threshold transgressions with sections of said surface.

8. The apparatus of claim 1, further comprising a lens positioned between the detecting means and the web, the lens serving to direct a portion of the light reflected from the smooth reflective surface of the web onto the array of photosensitive elements.

9. A system for analyzing light intensities of light reflected from a moving smooth reflective surface of a specimen, comprising:

a detector having a point light source positioned to direct light onto the surface and a sensor positioned to detect the light reflected from the surface, the sensor having a linear array of photosensitive elements that serve as an array of pixels and configured to generate a detection signal with information about the light intensities of the light reflected from the surface sensed by each photoresistive element; the smooth reflective surface moving along a path relative to the point light source and the array of photoresistive elements; and a processor coupled to the sensor, the processor configured to receive and analyze the detection signal to identify a sufficient number of pixels whose sensed light intensities transgress at least one threshold to warrant classification as an extraordinary reflection of light due to aberrational non-incidental reflection of light, said processor being capable of identifying whether said threshold is exceeded for a predetermined time period so as to be indicative of the presence of a crease along said web.

10. The system of claim 9, wherein the processor is configured to compare the sensed reflected light of each to two thresholds, one threshold being above an average light intensity, and the other threshold being below an average light intensity and to identify transgressions of either threshold.

11. The system of claim 9, wherein the sensor is a charged coupled device array.

12. The system of claim 9, wherein the detection signal is classified into timed segments, each timed segment being time allocated to a different grouping of photosensitive elements and thus a different portion of the surface of the specimen.

13. The system of claim 12, wherein the processor is configured to identify transgressions of the at least one threshold within each timed segment of the detection signal.

14. The system of claim 9, wherein an intensity of the light source is regulated such that the detection signal is adjusted to have a constant average voltage.

15. The system of claim 14, wherein the processor is configured to identify transgressions of two thresholds and the thresholds are established as deviations from the average voltage of the detection signal.

16. The system of claim 9, wherein the specimen is a web.

17. The system of claim 9, wherein the specimen is a recording tape.

18. The system of claim 17, wherein the recording tape is a video tape.

19. The system of claim 9, wherein a lens is positioned between the sensor and the specimen so as to direct light reflected from a segment of the specimen onto the sensor.

20. The system of claim 19, wherein the sensor is a CCD array, the specimen is a web and the lens directs a transverse segment of the web onto an entire length of the CCD array.

21. A system for analyzing light intensities of light reflected from a smooth reflective surface of a moving web, comprising:

a detector having a point light source positioned to direct light onto the surface and a sensor positioned to detect the light reflected from the surface, the sensor having an array of photosensitive elements that serve as an array of pixel elements and configured to generate a detection signal with information about the light intensities of the light reflected from the surface sensed by each pixel element; and a processor coupled to the sensor, the processor configured to receive and analyze the detection signal to identify a sufficient number of pixels whose sensed light intensities transgress either of two thresholds to warrant classification as an extraordinary reflection of light due to aberrational non-incidental reflection of light, one threshold being above an average light intensity, and the other threshold being below the average light intensity, said processor being capable of identifying whether said threshold is exceeded for a predetermined time period so as to be indicative of the presence of a crease along said web.

22. The system of claim 21, wherein the sensor is a charged coupled device array.

23. The system of claim 21, wherein the detection signal is classified into timed segments, each timed segment being time allocated to a different portion of the surface of the web.

24. The system of claim 21, wherein an intensity of the light source is regulated such that the detection signal is adjusted to have a constant average voltage.

25. The system of claim 24, wherein the thresholds are established as deviations from the average voltage of the detection signal.

26. The system of claim 21, wherein the web is a recording tape.

27. The system of claim 26, wherein the recording tape is a video tape.

28. The system of claim 21, wherein a lens is positioned between the sensor and the specimen so as to direct light reflected from a segment of the surface of the specimen onto the sensor.

29. The system of claim 28, wherein the sensor is a CCD array, the web is a recording tape and the lens focuses a transverse segment of the recording tape onto an entire length of the CCD array.

30. A method of evaluating a smooth reflective surface of a specimen, comprising the steps of:

directing light from a point source of light onto the surface of the specimen;

sensing light reflected from the surface with a sensor having an array of photosensitive elements;

moving the surface along a path relative to the point source of light and the sensor;

generating a detection signal with information about intensities of reflected light sensed by each photosensitive element;

processing said detection signal to determine whether any of said photosensitive elements sensed an intensity of reflected light that transgresses at least one threshold due to reflection of aberrational non-incidental light and to generate threshold transgression signal;

processing said threshold transgression signal to determine whether at least a preselected sufficient number of said photosensitive elements sensed an intensity of reflected light that transgressed the at least one threshold; and generating a signal with information regarding whether a sufficient number of said photosensitive elements transgressed the at least one threshold.

31. The method of claim 30, comprising the further step of sequencing through said array of photosensitive elements to generate said detection signal.

32. The method of claim 30, wherein said step of processing said detection signal comprises determining whether any of said photosensitive elements sensed an intensity of reflected light that transgresses either of two thresholds, a lower threshold and an upper threshold.

33. The method of claim 30, comprising the further step of regulating a light source so that detection signal indicates the sensing of a preselected average light intensity.

34. The method of claim 31, comprising the further step of generating timing signals that correlate said indications of threshold transgressions in said threshold transgression signal with the photosensitive elements sensing said threshold transgressions.

35. The method of claim 30, wherein said specimen is a web.

36. The method of claim 35, wherein said web is a recording tape.

37. The method of claim 36, wherein said recording tape is a video tape.

38. The method of claim 30, comprising the further step of using a lens to direct light reflected from a preselected portion of the surface onto the array of photosensitive elements.

* * * * *